(12) United States Patent
Ramirez-Delgado

(10) Patent No.: US 7,469,801 B2
(45) Date of Patent: Dec. 30, 2008

(54) AUTOMATIC MACHINE FOR DOSING WATER AND DENTAL ALGINATE

(76) Inventor: Roberto Alfredo Ramirez-Delgado, Industria del Plastico No. 2113, Zapopan Industrial Norte, 45132 Zapopan, Jalisco (MX)

( * ) Notice: Subject to any disclaimer, the term of this patent is extended or adjusted under 35 U.S.C. 154(b) by 621 days.

(21) Appl. No.: 11/105,572

(22) Filed: Apr. 14, 2005

(65) Prior Publication Data
US 2006/0231573 A1 Oct. 19, 2006

(51) Int. Cl.
*B67D 5/08* (2006.01)
(52) U.S. Cl. .............................. 222/52; 222/61; 222/63; 222/64; 222/129; 222/135; 222/161; 222/258; 222/333; 222/413
(58) Field of Classification Search .................. 222/52, 222/61, 63–64, 129, 135, 158–159, 161–162, 222/226–227, 261–263, 333–334, 258, 643, 222/631–632, 196, 198, 236, 241, 410–413, 222/233, 238; 433/27, 28
See application file for complete search history.

(56) References Cited

U.S. PATENT DOCUMENTS

| | | | | |
|---|---|---|---|---|
| 4,490,046 A | * | 12/1984 | Guibert | 366/76.4 |
| 4,691,846 A | * | 9/1987 | Cordell et al. | 222/198 |
| 5,051,528 A | | 9/1991 | Naujokas et al. | |
| 5,325,638 A | * | 7/1994 | Lynn | 451/39 |
| 6,120,567 A | * | 9/2000 | Cordell et al. | 48/197 R |
| 6,145,709 A | * | 11/2000 | Hogan et al. | 222/278 |
| 6,309,570 B1 | * | 10/2001 | Fellabaum | 264/40.1 |
| 6,580,005 B1 | | 6/2003 | Yazaki et al. | |
| 2006/0231570 A1 | * | 10/2006 | Ramirez-Delgado | 222/64 |

FOREIGN PATENT DOCUMENTS

EP 1 227 075 A1 7/2002
EP 0 973 715 B1 8/2002

* cited by examiner

*Primary Examiner*—Frederick C. Nicolas
(74) *Attorney, Agent, or Firm*—Browdy and Neimark, P.L.L.C.

(57) ABSTRACT

An automatic machine for dosing water and dental alginate is disclosed. The machine comprises a pressurized water container and a dental alginate container. In the automatic machine, a predetermined amount of each of those substances is transported from its respective container to a dosing point. During operation of the automatic machine, dental alginate is moved inside the alginate container with the purpose of bringing down residues of alginate adhered to the internal walls of the alginate container. In addition, the automatic machine comprises a control unit with a memory that stores dosing programs, this memory may be programmed in order to handle dental alginate of different manufactures.

22 Claims, 4 Drawing Sheets

AUTOMATIC MACHINE FOR DOSING WATER AND DENTAL ALGINATE

TECHNICAL FIELD

This invention relates to the techniques used to design apparatus and equipment for dental purposes, and more specifically, relates to an automatic machine for dosing water and dental alginate.

BACKGROUND OF THE INVENTION

In order to take dental impressions, it is well known that dentists use an alginate gel poured into a mold that is positioned around the teeth of a patient. Once the gel has solidified into the mold, the same is extracted from the mouth of the patient, thus obtaining the desired dental impression.

With regard to the above, alginate gel is obtained from a mixture of water and alginate powder. It is important mentioning that said powder is very fine and is obtained from marine algae as its main raw material. When dental alginate is mixed with water, a gelification reaction occurs between such substances.

When a dentist or his assistant is preparing a mixture of water and alginate, he must be careful of exactly measuring predetermined amounts of such ingredients in order to form a gel having the desired consistency, which allows the dentist to work easily with the gel. Therefore, alginate producers recommend and indicate in their products the exact amounts of water and alginate to be used in order to prepare adequate mixtures. In fact, most of the alginate producers include in their packages two measuring devices, one for alginate and one for water, with the purpose of measuring such required amounts. The measuring devices are containers, spoons, etc., most of them having printed marks that indicate the dentist the amount of water or alginate being measured.

Moreover, some alginate producers often include kits for preparing mixtures, one of said kits is disclosed in the U.S. Pat. No. 5,709,467, incorporated herein by reference. Particularly, the invention of this patent is a mixing pouch, in which water and alginate are mixed by hand. In a preferred embodiment of the invention of said patent, a predetermined amount of alginate is previously included into the pouch, therefore a dentist only have to add water into the pouch and mix the content. However, this document does not mention how to measure exactly the required amounts of alginate. In addition, if a package of alginate is provided with a set of pouches, the volume of the package will be increased.

Measuring water and alginate is not an easy and fast work for dentists, since there are some cares that must be taken, for example, due to the tendency of alginate powder to form lumps, the alginate package must be shaken prior to extract the alginate with the corresponding measuring device. Alginate has hydrophilic properties, therefore, it is recommended to store the packages of alginate in dry places in order to maintain the properties of this substance.

With regard to the above, if a dentist uses lumps of alginate, it is very probable that he will measure an incorrect amount of alginate and the resulting mixture will have a poor performance for taking dental impressions. This problem also occurs when a dentist uses amounts of water distinct to those recommended by the alginate producer.

In addition, when dentists handle alginate powder, there are cleaning problems on the working area, inasmuch as alginate powder is very volatile and tends to float in the air. This problem is more frequent when an excess of alginate is extracted from the package using such measuring devices, inasmuch as some part of the excess will be inevitably deposited on the working area when the dentist tries to return the excess to the package. On the other hand, dentists must be careful of avoiding alginate to be contaminated by dust or substances contained in the air when a package is opened.

From the foregoing, it can be observed that a dentist or his assistant has to spend many time in measuring the required amounts of water and alginate and he has to adequately handle alginate. In the prior art, there is a lack of devices or machines that facilitate the work of preparing mixtures for taking dental impressions. In other words, nowadays, there is not a machine for dosing water and alginate, which covers all the dentist requirements in this measuring and handling activity.

SUMMARY OF THE INVENTION

A solution has been developed to avoid the problems of measuring and dosing water and alginate, which are used in a mixture for taking dental impressions; this solution is particularly related to an automatic machine for dosing water and dental alginate according to predetermined amounts. The automatic machine of the present invention comprises:
a) a pressurized water container in which water is stored;
b) means for pressuring said water container;
c) a valve being in flow connection with said water container; said valve allowing water to flow from said pressurized water container to a water dosing point;
d) an alginate container in which dental alginate is stored;
e) means for vibrating said alginate container;
f) means for transporting the dental alginate from the bottom of said alginate container to an alginate dosing point; and,
g) a control unit being electrically connected to: i) said valve, ii) said vibrating means, and iii) said transporting means.

This combination of elements, which together form the automatic machine for dosing water and dental alginate of the present invention, allow a user to obtain water an dental alginate according to predetermined amounts, which are exactly measured by the machine. More particularly, when the user wishes to obtain water and dental alginate from the automatic machine, he only has to operate said control unit, which in turn opens and closes said valve in order to dose a predetermined amount of water from said water container to the water dosing point; then, said control unit operates the vibrating means in order to move the dental alginate inside said alginate container and, immediately after and keeping in operation said vibrating means, said control unit operates said transporting means in order to carry a predetermined amount of dental alginate from the bottom of said alginate container to the alginate dosing point.

Once the predetermined amount of alginate has been dosed, said control unit stops the operation of said vibrating means and changes the direction of operation of the transporting means in order to return any alginate amount remaining in said transporting means to the alginate container.

In a preferred embodiment of the invention, the pressurized water container includes a hermetic lid for maintaining the pressure therein. In addition, the alginate container has the form of a hopper and it is made of polyethylene, this polymer avoids alginate to be adhered on the internal walls of the alginate container. The vibrating means are a pair of vibrating motors being in contact with the external surface of the bottom of said alginate container. The vibrating means moves the dental alginate inside the alginate container; this movement has the purpose of conducting alginate to the bottom of this container, where alginate is received by the transporting means. Furthermore, the vibrating motion has the objective of
} bringing down residues of alginate adhered to the internal walls of the alginate container, if any.

In the preferred embodiment, the transporting means comprises an arrangement of a helical worm, an electric motor and a tube for housing the helical worm, so that when the electric motor rotates the helical worm, the dental alginate is carried from the alginate container to the alginate dosing point.

The control unit includes a memory that stores dosing programs, which may be selected by the user using keys included in said control unit.

In a second preferred embodiment of the invention, the memory is programmable. This feature allows the user to work with dental alginate supplied by different manufactures, more specifically; the user may modify the amount of water to be dosed by the machine according to the specific properties of dental alginate.

In an alternative embodiment of the present invention, the automatic machine further comprises:

h) a first sensor associated to said alginate container and being in electrical connection with said control unit, the first sensor generating a first signal which is transmitted to said control unit, which in turn indicates the user the alginate powder amount available inside said alginate container, and, i) a second sensor associated to the water container and being in electrical connection with said control unit, the second sensor generating a second signal which is transmitted to said control unit, which in turn indicates the user the water amount available in said water container;

If the level of water or dental alginate is lower than a minimum level, the control unit emits a visual or sound alarm As it can be observed from the foregoing, it is an object of the present invention to provide an automatic machine for dosing water and dental alginate, wherein the dosed amounts of these substances are exactly measured by the machine.

Another object of the present invention is to provide an automatic machine for dosing water and dental alginate, which allow the dentists to save time in the whole process of obtaining a dental impression.

Yet, it is an object of the present invention to provide an automatic machine for dosing water and dental alginate, wherein the alginate is stored and dosed in optimal conditions.

BRIEF DESCRIPTION OF THE DRAWINGS

The novel aspects that are considered characteristic of the present invention are particularly set forth in the appended claims. The invention itself, however, both as to its structure and to its method of operation, together with additional objects and advantages thereof, will best be understood from the following description of a preferred embodiment thereof, when read in relation to the appended drawings, in which:

DETAILED DESCRIPTION OF THE INVENTION

Figure 1:
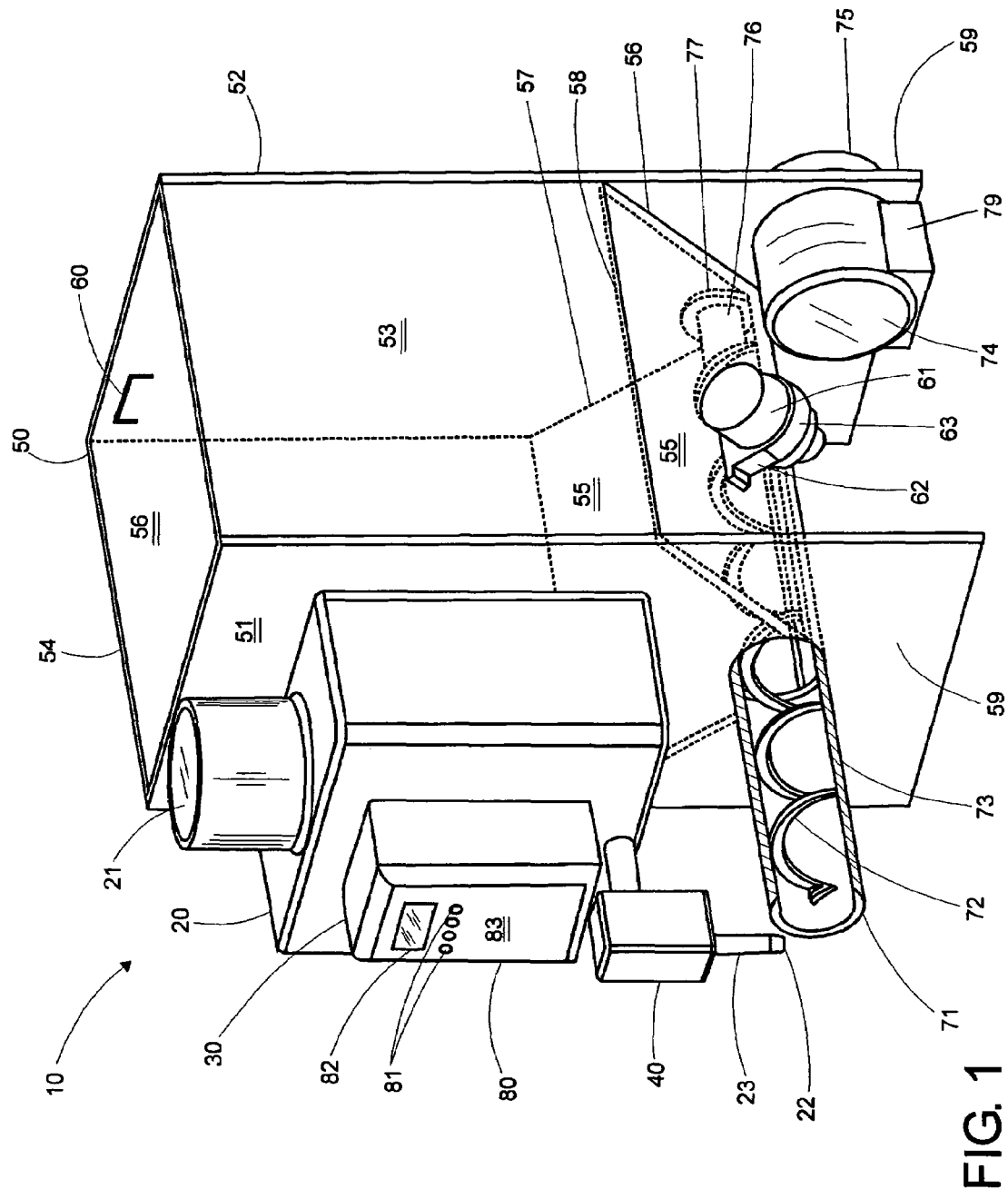
FIG. 1 is a perspective and fragmentary view of an automatic machine for dosing water and dental alginate, which is built in accordance with the principles of a preferred embodiment of the present invention.
Figure 2:
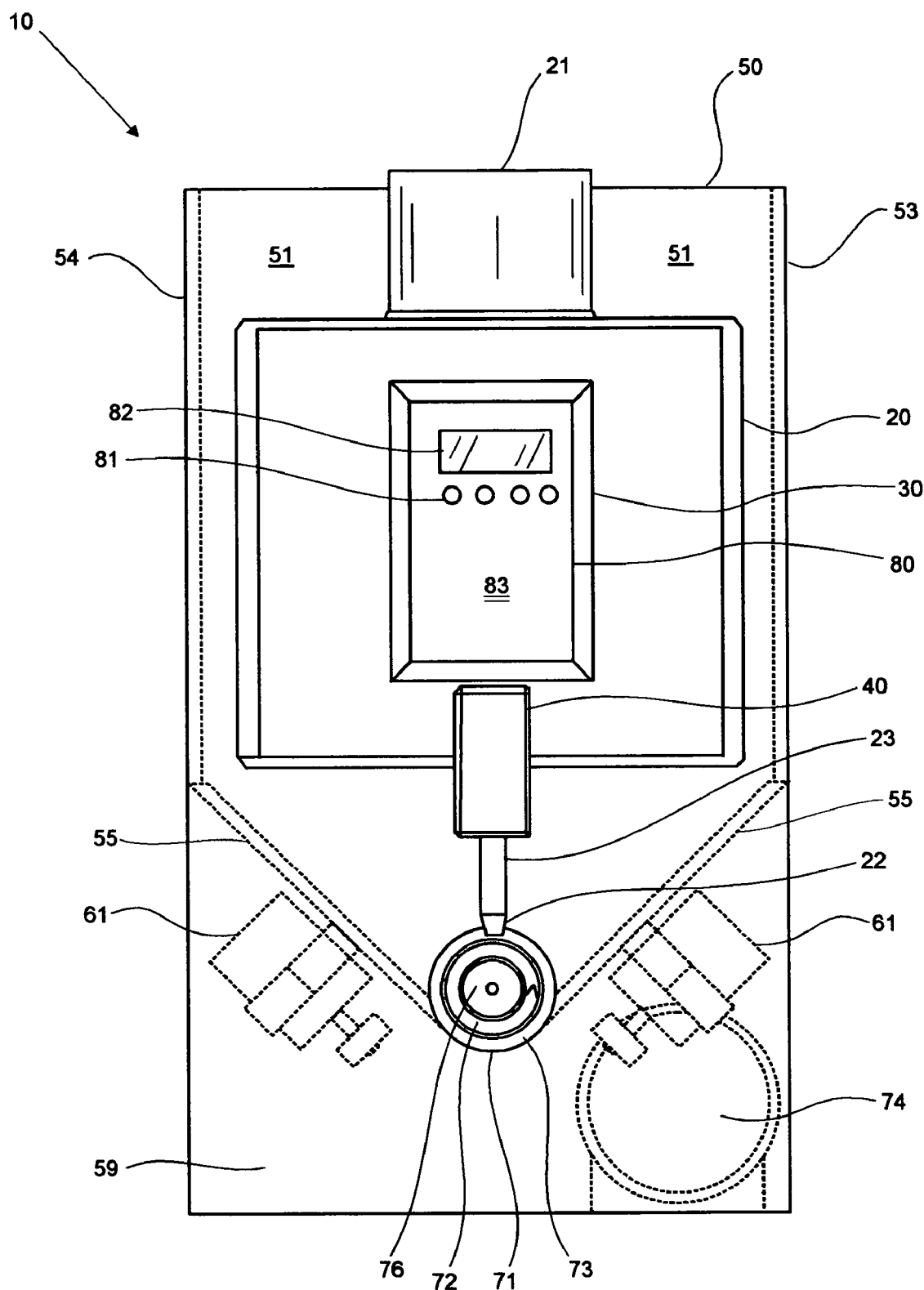
FIG. 2 is a front view of the automatic machine for dosing water and dental alginate shown in FIG. 1.
Figure 3:
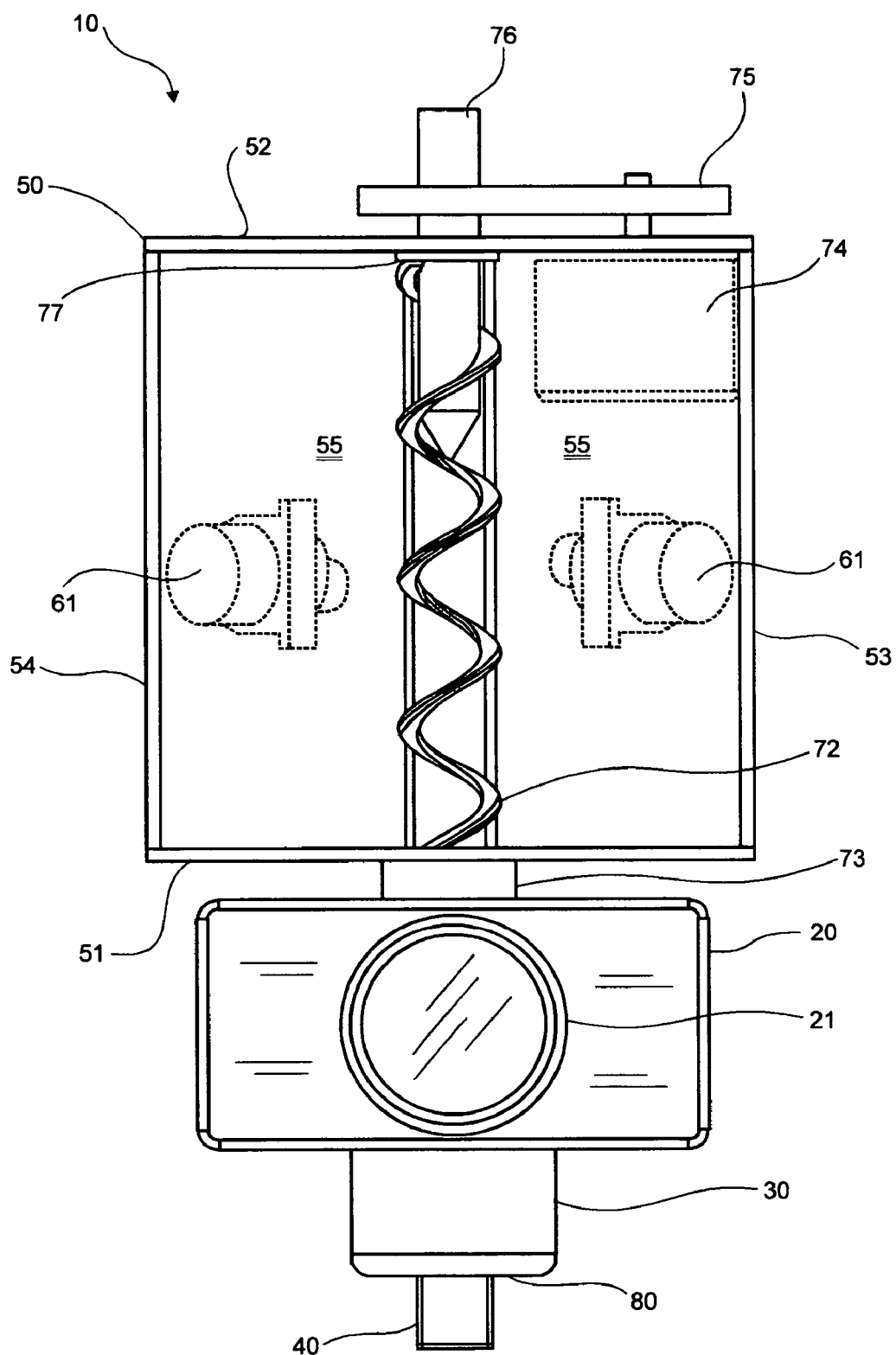
FIG. 3 is a top plan view of the automatic machine for dosing water and dental alginate shown in FIG. 1.

With specific reference to FIGS. 1 to 3 of the appended drawings, these show an automatic machine for dosing water and dental alginate 10, built in accordance with the principles of a preferred embodiment of this invention, which should be considered as illustrative but not restrictive thereof. The automatic machine 10 of this preferred embodiment comprises a pressurized water container 20, in which water is stored; the pressurized water container 20 is pressurized by pressure means, that, in this preferred embodiment, is an air pump 30 which supplies air to the inside of the pressurized water container 20, thus forming and air chamber above the surface of water. Preferably, the air pump is a diaphragm type pump, such as those used in house aquariums.

To maintain the pressure inside the pressurized water container 20, the same includes a hermetic lid 21, which, in addition, can be removed in order to add water inside the pressurized water container 20 when the level of this liquid is low therein.

In FIG. 1, it can be observed that the automatic machine 10 is provided with a valve 40 in flow connection with said pressurized water container 20. During operation of the automatic machine 10, the valve 40 allows water to flow from the pressurized water container 20 to a water dosing point 22. In this regard, the valve 40 is preferably an electrovalve and the water dosing point 22 is the output of a nozzle 23 being, of course, in flow connection with the valve 40. The elements disclosed have the function of dosing the exact amount of water required by a user.

On the other hand, the automatic machine for dosing water and dental alginate 10 comprises a series of elements for handling and dosing the required amount of dental alginate.

With regard to the above, from FIGS. 1 to 3, it can be observed that the automatic machine 10 comprises an alginate container 50 having the form of a rectangular hopper with a front wall 51, a rear wall 52, two lateral walls 53, 54, a bottom 55 and a lid 56 closing the alginate container 50. The bottom 55 is formed by two sloping sections 57 and 58, each of them extending from the inferior edge of the lateral walls 53, 54 to the longitudinal middle line of the alginate container 50, where the sloping sections 57 and 58 join each other.

The lid 56 hermetically closes the alginate container 50 and is hingely connected thereto, if the level of alginate inside the alginate container 50 is low, the user may add alginate therein opening the lid 56 with the handle 60 that is attached to the lid 56.

Moreover, with the purpose of constructing an automatic machine for dosing water and dental alginate 10 very compact in size, the front wall 51 and the rear wall 52 have each a vertical extension 59 formed integrally therewith and the pressurized water container 20 is joined to the front wall 51 of the alginate container 50. Each vertical extension 59 runs downwardly from the bottom 55 of the alginate container 50 in order to form supporting members for the automatic machine 10.

It is worth mentioning that the alginate container 50 is preferably made of polyethylene, this polymer avoids alginate to be adhered on the internal walls of the alginate container 50, therefore, old alginate is never kept inside the alginate container 50.

The above disclosed form of the alginate container 50 and the preferred material used for its construction allow keeping and dosing dental alginate in optimal conditions. Preferably, alginate container 50 may store from about 1 pound (0.454 kg) to about 7 pounds (3.18 kg) of dental alginate, more preferably it may store about 5 pounds (2.28 kg), this capacity of the alginate container 50 allow a dentist to work for several weeks without refilling the alginate container 50.

The automatic machine for dosing water and dental alginate 10 is also provided with means for vibrating the alginate container 50, in the preferred embodiment illustrated in FIGS. 1-3, the vibrating means comprises a pair of electric vibrator motors 61, each of them being in contact with the external surface of the bottom 55 of the alginate container 50. The electric vibrator motors 61 are symmetrically located on the external surface of the bottom 55, and each of them is put in contact thereto by means of a base 62 firmly attached to the alginate container 50; the base 62 includes a holder 63 surrounding the electric vibrator motor 61. In FIGS. 2 and 3, the electric vibrator motors 61 are represented in dashed lines, however, these figures allow to observe how such electric vibrator motors 61 are in contact with the bottom 55 of the alginate container 50.

Specifically, the vibrating means have the objective of moving alginate inside the alginate container 50, as well as, having the objective of bringing down residues of alginate adhered to the internal walls of the alginate container 50, if any. To accomplish such objectives, each of the electric vibrator motors 61 generates high frequency vibrations that are transmitted to the dental alginate through the bottom 55 of the alginate container 50. In this regard, alginate may also be moved inside the alginate container 50 by means of a mixer or a shaking mechanism connected to the alginate container 50, nevertheless, these arrangements will be more complex.

Alginate is transported from the bottom 55 of the alginate container 50 to an alginate dosing point 71 located outside the alginate container 50 by transporting means, which in the preferred embodiment of the invention, comprises:

- a helical worm 72 disposed vertically along the bottom 55 of the alginate container 50 and rotary mounted thereto; the helical worm 72 has a portion running outside of the alginate container 50 and ending at the alginate dosing point 71;
- a tube 73 for housing the portion of the helical worm 72 which is outside of said alginate container 50; one end of the tube 73 being received in said alginate container 50; and,
- an electric motor 74 operatively connected to said helical worm 72 in order to rotate the same inside the alginate container 50 and the tube 73.

Preferably, the electric motor 74 is connected to the helical worm by means of a transmission belt 75 and is supported by a motor base 79 joined to the alginate container 50. In FIGS. 2 and 3 the electric motor 74 is represented in dashed lines and is preferably a step motor with a step resolution from about 1.0° to about, 2.0°, and more preferably of 1.5°.

Figure 4:
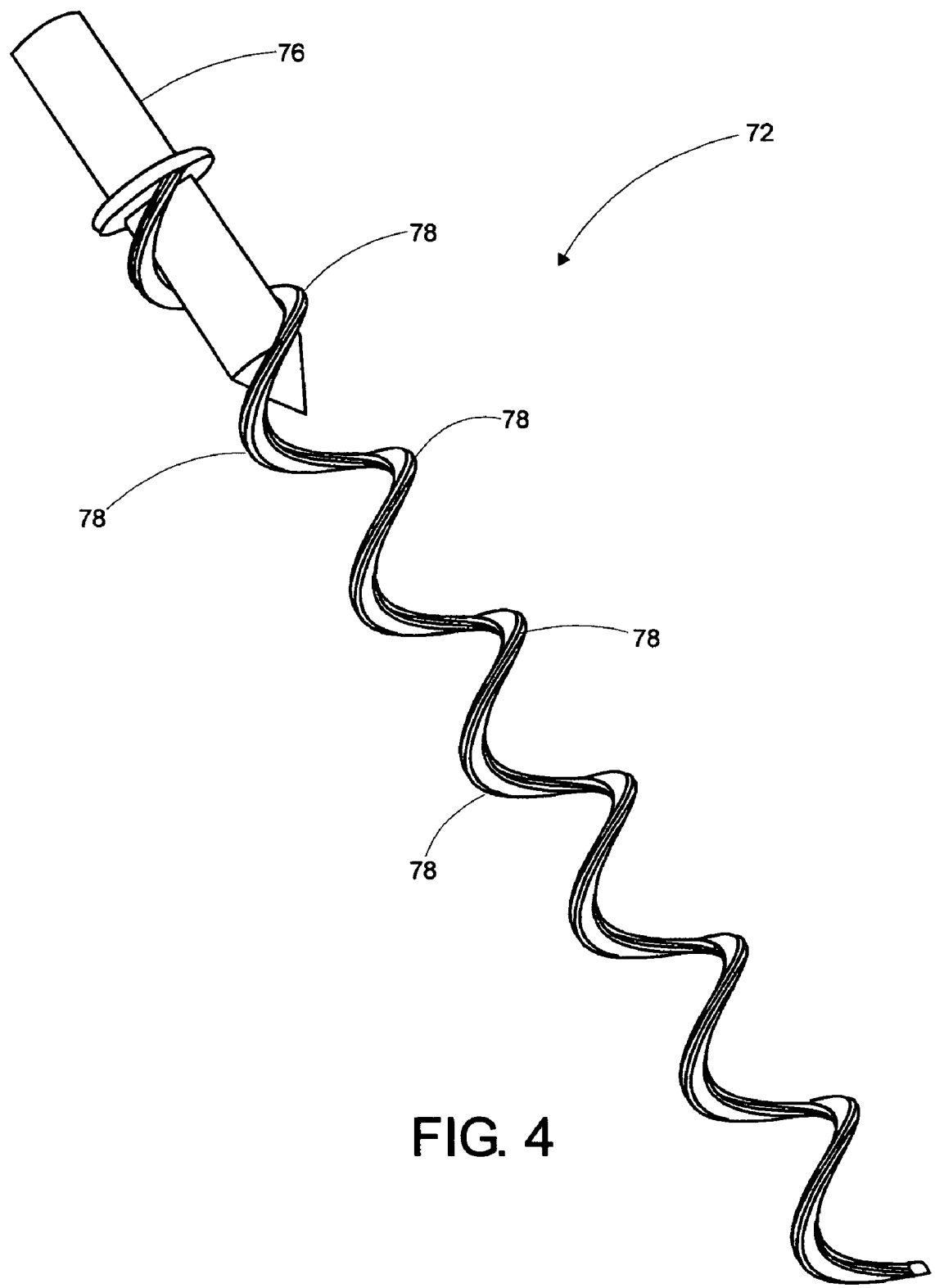
FIG. 4 is a perspective view of the helical worm which forms part of the transporting means included in the automatic machine for dosing water and dental alginate shown in FIG. 1.

For mounting the helical worm 72 to the alginate container 50, an end of the helical worm 72 is firmly joined to a rotary base 76 that is received in a bearing 77 disposed on the rear wall 52 of the alginate container 50, such rotary base 76 can be easily observed in FIG. 4, which shows a perspective view of the helical worm 72 provided with blades 78. In this regard, the blades of helical worm 72 partially cover the cross section of the tube 73. This feature of the helical worm 72 along with the step resolution of the step motor allow to transport an exact amount of alginate from the alginate container 50 to the alginate dosing point 71 defined by the free end of the tube 73. In this preferred embodiment, the alginate dosing point 71 is located under the water dosing point 22, thus, when the automatic machine 10 is in operation, a dentist may easily collect both substances in a separate vessel and mix them.

This preferred configuration for the transporting means allow dentists to handle and dose alginate in the exact amounts for preparing an adequate gel. Other configurations for the transporting means may also be possible, such a conveyor belt which extracts and transports a predetermined volume of alginate powder from the alginate container 50, however, this solution is not so efficient as the arrangement of transporting means previously disclosed.

In FIGS. 1-3, it can be observed that the automatic machine for dosing water and dental alginate 10 further comprises a control unit 80 electrically connected to: i) said valve 40, ii) the electric vibrator motors 61, and iii) the electric motor 74 of the transporting means. When the user wishes to obtain water an dental alginate, he only has to operate said control unit 80, which in turn opens and closes said valve 40 in order to dose a predetermined amount of water from said water container 20 to the water dosing point 22; then, said control unit 80 operates the electric vibrator motors 61 in order to move the dental alginate inside said alginate container 50 and, immediately after and keeping in operation said electric vibrator motors 61, the control unit 80 operates the electric motor 74 that make the helical worm 72 to rotate inside the alginate container 50 in order to transport a predetermined amount of dental alginate from the bottom 55 of said alginate container 50 to the alginate dosing point 71.

Once the predetermined amount of alginate has been dosed, said control unit 80 stops the operation of the electric vibrator motors 61 and changes the operation direction of the electric motor 74, in order to return any alginate amount remaining in the tube 73 to the alginate container 50. This returning movement of the electric motor 74 makes alginate to be lightly compacted inside the alginate container 50, this function of the automatic machine 10 has the object of not provoking an erroneous dose each time that the automatic machine 10 is put in operation. Preferably, when the electric motor 74 is a step motor, it rotates from about 3° to about 5° when changing the operation direction thereof.

In order to perform the controlled operations of the automatic machine 10, the control unit 80 comprises:

- a memory which stores dosing programs, each of them corresponding to a specific ratio between the amounts of water and dental alginate to be dosed;
- a control panel 83 having a plurality of keys 81, each of said keys 81 corresponding to a specific dosing program that the user may select; and,
- a display 82, which is in electrical connection to the keys and the memory, the display 82 shows the user the specific dosing program being performed by the automatic machine 10.

In a second preferred embodiment of the invention, the memory of the control unit 80 is programmable in order that the user may vary the amount of water to be dosed with respect to the amount of dental alginate. This feature for the memory implies an advantage for the user, inasmuch as he can use alginate of different manufactures. For the dentist, it is known that the properties of alginate varies from one producer to another.

In an alternative embodiment of the present invention which is not shown in the appended drawings, the automatic machine 10 further comprises: a first sensor associated to said alginate container 50 and being in electrical connection with said control unit 80, the first sensor generating a first signal which is transmitted to said control unit 80, which in turn indicates the user the alginate powder amount available inside said alginate container 50. Likewise, in this alternative embodiment, the automatic machine 10 comprises a second sensor associated to the water container 20 and being in electrical connection with said control unit 80, the second sensor generating a second signal which is transmitted to said control unit 80, which in turn indicates the user the water amount available in said water container 20. Therefore, if the level of water or dental alginate is lower than a minimum level, the control unit 80 emits a visual or sound alarm.

In accordance with that previously described and as illustrated in the attached drawings, it may be seen that the automatic machine used for dosing water and dental alginate has been designed to handle and dose exact quantities of such substances, consequently, the dentists save time and they will be sure of preparing an adequate mixture for taking dental impressions. The apparatus is compact in size and may handle alginate of different manufactures, so it will be obvious to any expert in this area that the embodiments described previously are only illustrative and not limit the invention, as there are numerous modifications that may be made, such as the form of the alginate container, the location of vibrator means with respect to the alginate container, and others, without this altering the essential scope and function of the invention.

Even though some specific embodiments of this invention have been described and illustrated, we should emphasize that there are numerous modifications that may be made. Therefore, this invention should not be considered as restrictive, except for that which the prior art requires, and for the attached claims.

What is claimed is:

1. An automatic machine for dosing water and dental alginate comprising:
    a) a pressurized water container in which water is stored;
    b) means for pressuring said pressurized water container;
    c) a valve being in flow connection with said pressurized water container; said valve allowing the water to flow from said pressurized water container to a water dosing point;
    d) an alginate container in which dental alginate is stored; said alginate container having a bottom provided with an external surface;
    e) means for vibrating said alginate container;
    f) means for transporting the dental alginate from the bottom of said alginate container to an alginate dosing point which is outside of said alginate container; and,
    g) a control unit being electrically connected to:
    i) said valve, ii) said vibrating means, and ii) said transporting means;
        wherein said control unit opens and closes said valve in order to dose a predetermined amount of the water from said pressurized water container to the water dosing point; then, said control unit operates said vibrating means in order to move the dental alginate inside said alginate container and, immediately after and keeping in operation said vibrating means, said control unit operates said transporting means in order to carry a predetermined amount of the dental alginate from the bottom of said alginate container to the alginate dosing point; once the predetermined amount of the alginate has been dosed, said control unit stops operation of said vibrating means and operates said transporting means in order to return any amount of the alginate remaining in said transporting means to said alginate container.

2. An automatic machine for dosing water and dental alginate, according to claim 1, wherein said pressurized water container includes a hermetic lid.

3. An automatic machine for dosing water and dental alginate, according to claim 1, wherein said pressure means is an air pump which supplies air to said pressurized water container.

4. An automatic machine for dosing water and dental alginate, according to claim 3, wherein the air pump is a diaphragm type pump.

5. An automatic machine for dosing water and dental alginate, according to claim 1, wherein said valve is an electrovalve and the dosing point is a nozzle being in flow connection with said valve.

6. An automatic machine for dosing water and dental alginate, according to claim 1, wherein said alginate container has a form of a rectangular hopper with a front wall, a rear wall, two lateral walls, and a lid for closing said alginate container; wherein the bottom being formed by two sloping sections that join each other.

7. An automatic machine for dosing water and dental alginate, according to claim 6, wherein the lid hermetically closes said alginate container and is hingely connected thereto.

8. An automatic machine for dosing water and dental alginate, according to claim 7, wherein the lid includes a handle attached thereto for opening said lid.

9. An automatic machine for dosing water and dental alginate, according to claim 6, wherein the front wall and the rear wall have each a vertical extension formed integrally therewith, each vertical extension running downwardly from the bottom of said alginate container in order to form supporting members for the automatic machine.

10. An automatic machine for dosing water and dental alginate, according to claim 1, wherein said alginate container is made of polyethylene.

11. An automatic machine for dosing water and dental alginate, according to claim 1, wherein said alginate container stores from 1 pound to 7 pounds of the dental alginate.

12. An automatic machine for dosing water and dental alginate, according to claim 1, wherein said vibrating means comprises a pair of electric vibrator motors, each of them being in contact with the external surface of the bottom of said alginate container.

13. An automatic machine for dosing water and dental alginate, according to claim 12, wherein the electric vibrator motors are symmetrical located on the external surface of the bottom of said alginate container, and each of them is put in contact thereto by means of a base firmly attached to the alginate container, the base including a holder that surrounds the corresponding electric vibrator motor.

14. An automatic machine for dosing water and dental alginate, according to claim 12, wherein each of the electric vibrator motors generates high frequency vibrations that are transmitted to the dental alginate through the bottom of said alginate container.

15. An automatic machine for dosing water and dental alginate, according to claim 1, wherein said transporting means comprises:
    a helical worm vertically disposed along the bottom of said alginate container and rotary mounted thereto; the helical worm having a portion which runs outside of said alginate container and ends at the alginate dosing point;
    a tube for housing the portion of the helical worm which is outside of said alginate container; the tube having two ends, one of them being received in said alginate container; and the other end being a free end; and,
    an electric motor operatively connected to the helical worm in order to rotate the same inside the alginate container and the tube.

16. An automatic machine for dosing water and dental alginate, according to claim 15, wherein the electric motor is connected to the helical worm by a transmission belt and is supported by a motor base joined to said alginate container.

17. An automatic machine for dosing water and dental alginate, according to claim 15, wherein the electric motor is a step motor with a step resolution from 1.0° to 2.0°.

18. An automatic machine for dosing water and dental alginate, according to claim 15, wherein the alginate dosing point is defined by the free end of the tube.

19. An automatic machine for dosing water and dental alginate, according to claim 1, wherein the water dosing point is above of the alginate dosing point.

20. An automatic machine for dosing water and dental alginate, according to claim 1, wherein the control unit comprises:
- a memory which stores dosing programs, each of them corresponding to a specific ratio between the amounts of the water and the dental alginate to be dosed;
- a control panel having a plurality of keys, each of said keys corresponding to a specific dosing program that can be selected; and,
- a display, which is in electrical connection to the keys and to the memory, the display showing the specific dosing program being performed by the automatic machine.

21. An automatic machine for dosing water and dental alginate, according to claim 20, wherein the memory of said the control unit is programmable in order to vary the amount of the water to be dosed with respect to the amount of the dental alginate.

22. An automatic machine for dosing water and dental alginate, according to claim 1, wherein the automatic machine further comprises:
- h) a first sensor associated to said alginate container and being in electrical connection with said control unit, the first sensor generating a first signal which is transmitted to said control unit, which in turn indicates the alginate amount available inside said alginate container; and,
- i) a second sensor associated to the water container and being in electrical connection with said control unit, the second sensor generating a second signal which is transmitted to said control unit, which in turn indicates the water amount available in said water container; so that, if the level of the water or the dental alginate is lower than a minimum level, said control unit emits a visual or sound alarm.

* * * * *